United States Patent [19]
Lee et al.

[11] Patent Number: 6,007,799
[45] Date of Patent: Dec. 28, 1999

[54] CLEAR COSMETIC GEL COMPOSITION

[75] Inventors: Wilson Lee, Bloomfield; Kathy Potechin, Short Hills; Robert J. Bianchini, Belle Mead; Peter Hilliard, Jr., Far Hills, all of N.J.

[73] Assignee: Colgate Palmolive Company, New York, N.Y.

[21] Appl. No.: 08/689,814

[22] Filed: Aug. 14, 1996

Related U.S. Application Data

[60] Provisional application No. 60/002,509, Aug. 18, 1995.

[51] Int. Cl.$^6$ .............................. A61K 7/32; A61K 7/00
[52] U.S. Cl. .............................. 424/65; 424/66; 424/67; 424/68; 424/400; 424/401
[58] Field of Search ................................. 424/65, 66, 67, 424/68, 400, 401

[56] References Cited

U.S. PATENT DOCUMENTS

| | | | |
|---|---|---|---|
| 2,857,315 | 10/1958 | Teller | 424/65 |
| 2,900,306 | 8/1959 | Slater | 424/65 |
| 2,933,433 | 5/1960 | Teller et al. | 424/65 |
| 2,970,083 | 1/1961 | Bell | 424/65 |
| 3,259,545 | 7/1966 | Teller | 424/65 |
| 4,265,878 | 5/1981 | Keil | 424/68 |
| 4,280,994 | 7/1981 | Turney | 424/68 |
| 4,322,400 | 3/1982 | Yuhas | 424/59 |
| 4,382,079 | 5/1983 | Marschner | 424/65 |
| 4,383,988 | 5/1983 | Teng et al. | 424/68 |
| 4,414,200 | 11/1983 | Murphy et al. | 424/63 |
| 4,673,570 | 6/1987 | Soldati | 424/65 |
| 4,822,620 | 4/1989 | Chamberlain et al. | 426/2 |
| 4,900,542 | 2/1990 | Parrotta et al. | 424/66 |
| 4,937,069 | 6/1990 | Shin | 424/66 |
| 4,944,938 | 7/1990 | Potini | 424/68 |
| 4,948,578 | 8/1990 | Burger et al. | 424/68 |
| 5,069,897 | 12/1991 | Orr | 424/66 |
| 5,102,656 | 4/1992 | Kasat | 424/66 |
| 5,162,378 | 11/1992 | Guthauser | 514/785 |
| 5,456,906 | 10/1995 | Powell et al. | 424/66 |
| 5,587,153 | 12/1996 | Angelone, Jr. et al. | |
| 5,863,525 | 1/1999 | Angelone, Jr. et al. | |
| 5,925,338 | 7/1999 | Karassik et al. | |

FOREIGN PATENT DOCUMENTS

| | | |
|---|---|---|
| 373499 | 6/1990 | European Pat. Off. . |
| WO 91 08732 | 6/1991 | WIPO . |
| WO 92 05767 | 4/1992 | WIPO . |

*Primary Examiner*—Shelley A. Dodson
*Attorney, Agent, or Firm*—Rosemary M. Miano; William I. Solomon; Richard J. Ancel

[57] ABSTRACT

Disclosed is a clear cosmetic gel composition in the form of a water-in-oil emulsion, and methods of forming and of using the composition. The composition has a water-based phase containing water, a cosmetically active ingredient, and at least one coupling agent; and an oil-based phase containing a material having a refractive index in the range of 1.40–1.50, silicone fluids and an alkoxylated, alkyl substituted siloxane surface active agent (e.g., dimethicone copolyol). The composition has a refractive index in a range of 1.4026 to 1.4150. Where the cosmetically active ingredient is an antiperspirant active ingredient, the composition can be an antiperspirant gel (e.g., soft gel) composition. In the refractive index range of the present invention, increased amounts of, e.g., antiperspirant active ingredient, and other high-refractive-index materials providing cosmetic benefits, can be incorporated in the water and oil phases of the composition while still achieving a clear composition. The composition can also include polypropylene glycols (e.g., tripropylene glycol), as part of the water-based phase, to provide a composition having reduced tackiness and reduced whitening (decreased residue); this composition is also mild (reduced skin irritation potential) relative to comparable commercial products.

29 Claims, No Drawings

CLEAR COSMETIC GEL COMPOSITION

This application claims priority under 35 USC 119(e)(1) based on Provisional application Serial No. 60/002,509, filed Aug. 18, 1995.

BACKGROUND OF THE INVENTION

The present invention is directed to a clear cosmetic gel composition (for example, a clear soft gel antiperspirant composition) that is a water-in-oil emulsion. The composition of the present invention can include deodorant and/or antiperspirant active materials, to combat body malodor, for example, in axillary regions of the human body, by applying the composition to the human body (for example, to the skin, in axillary regions of the body).

The present invention is particularly directed to cosmetic gel compositions, including antiperspirant and deodorant gel compositions, that have reduced whitening and tack, and reduced skin irritation, and which can include increased amounts of the cosmetically active ingredient (for example, increased amounts of antiperspirant active ingredient), and can include other commercially beneficial materials, yet which can be provided as a clear gel product.

Antiperspirant products are well known in the art. Antiperspirants have appeared in the marketplace in varied dosage forms, such as sticks, soft solids, soft gels, roll-on, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes a continuous phase.

Of the above-referred-to dosage forms, the stick form is an example of a solid form, and the soft solid and soft gel are thickened forms which may or may not be solid (for example, under some circumstances, gels can flow). The stick form can be distinguished from a soft solid or soft gel in that, in a stick, the formulated product can retain its shape for extended time periods outside the package, the product not loosing its shape significantly (allowing for some shrinkage due to solvent evaporation). Adjustment of amounts of gelling or thickening agents can be used in order to form a soft gel or stick.

Soft gels or soft solids can be suitably packaged in containers which have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. No. 5,102,656 to Kasat, U.S. Pat. No. 5,069,897 to Orr, and U.S. Pat. No. 4,937,069 to Shin, each of which discloses such soft solids, including physical characteristics thereof such as viscosity and hardness. The contents of each of these three U.S. Patents are incorporated herein by reference in their entirety.

Recently, there has been significant activity in developing clear and translucent antiperspirant sticks and soft gels, particularly to provide sticks and soft gels having increased efficacy (for example, by providing increased amounts of the antiperspirant active in the sticks and soft gels), improved cosmetic characteristics (including reduced whitening, reduced residue and reduced tack), and reduced skin irritation potential (e.g., providing a product that is "mild").

Clear or translucent antiperspirant sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional active antiperspirant materials are acidic, much work has been involved in discovering suitable stabilizing or buffering agents to prevent or slow down acid attack on the acetal gelling agent. Such work has not been completely successful. Moreover, these clear or translucent antiperspirant sticks, containing the acetal gelling agent and including a solubilized active antiperspirant material, have the disadvantage of being inherently tacky. Thus, development work in connection with these clear or translucent antiperspirant sticks containing the acetal gelling agent has focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Various other gelling agents have been utilized in antiperspirant and deodorant products. For example, clear stick deodorant compositions have been available for some time. The clear deodorant sticks are generally produced by using stearate soaps as gelling agents for an alcoholic or glycolic solution of an antimicrobial agent and a fragrance. These deodorant products offer no antiperspirant protection (that is, these deodorant products do not reduce flow of perspiration from a human). Conventional antiperspirant active ingredients, which are acidic, are not ordinarily used with stearate soap gelling agents, because they are incompatible with the stearate soap gelling agents, due to the chemical interaction between the antiperspirant active material and the soap and consequent inactivation of the antiperspirant active material.

Gelling, for cosmetic compositions, may also be achieved through the use of cellulosic or algin-derived polymer materials. Most of these materials are incompatible with conventional antiperspirant active ingredients, at levels of the antiperspirant active ingredients required to obtain antiperspirant efficacy. Moreover, the polymer materials are unstable at the low pH normally encountered in antiperspirant products.

Concerning wax and soap-gelled sticks, see each of U.S. Pat. No. 4,382,079 to Marschner, U.S. Pat. No. 4,414,200 to Murphy, et al, U.S. Pat. No. 4,280,994 to Turney, U.S. Pat. No. 4,265,878 to Keil, U.S. Pat. No. 3,259,545 to Teller, U.S. Pat. No. 2,970,083 to Bell, U.S. Pat. No. 2,933,433 to Teller, et al., U.S. Pat. No. 2,900,306 to Slater, U.S. Pat. No. 2,857,315 to Teller, and U.S. Pat. No. 4,383,988 to Teng.

U.S. Pat. No. 4,948,578 to Burger, et al discloses a transparent antiperspirant stick which is an oil-in-water emulsion, containing specific amounts of an antiperspirant effective aluminum salt, a nonionic surfactant which is a $C_{11}$–$C_{18}$ fatty alcohol alkoxylated with from about 10 to about 20 moles ethylene oxide, a liquid oil immiscible with water, and water, the composition being free of any wax matrix. Illustratively, aluminum chlorhydrate is the antiperspirant salt, the nonionic surfactant is a $C_{11}$–$C_{18}$ alcohol ethoxylate, and the liquid oil component may be selected from emollient oils, volatile silicones and mixtures of these materials.

U.S. Pat. No. 4,944,938 to Potini discloses clear, nonalcoholic, quick drying, antiperspirant and deodorant gels, which are stable both at room temperatures and at higher temperatures, are non-stinging and leave no white residue on the skin, the gel not including gelling agents, waxes, clays, or monohydric alcohols having 2–8 carbon atoms. The gels use 3–5 carbon atom trihydric alcohols as coupling agents, these alcohols acting as solublizers in the system and keeping the system stable and clear. The gels can include an aluminum active salt; a volatile water-insoluble emollient, such as isostearyl benzoate; a soluble emollient such as cetyl ether; solubilizers such as propylene glycol and glycerine; volatile siloxanes; and water.

Some cellulosic materials, such as hydroxypropylcelluouse, among others, are compatible with polyvalent metal salts and have been used in the manufacture of clear lotions. These cellulosic materials, however, must be prepared with a high percentage of water or alcohol in order to insure solubilization of the active ingredient. The resulting formulations, in addition to a high irritation potential, are tacky and pituitous, and low in efficacy, when alcohol-based; and exhibit tackiness and a long drying time when water-based.

Clear or translucent antiperspirant soft gels (which have been dispensed from containers having the appearance of stick) have recently been marketed, consisting of viscous, high-internal-phase emulsions. These soft gels exhibit some advantages over the aforementioned sticks, particularly acetal-based clear sticks, in that the selection of formulation ingredients is less restricted (for example, water can be used), and often tack can be reduced significantly. Concerning these emulsions, note U.S. Pat. No. 4,673,570 to Soldati and U.S. Pat. No. 4,900,542 to Parrotta, et al. These two U.S. patents disclose clear gelled antiperspirant compositions free of waxes and conventional gelling agents, containing a volatile silicone fluid, a silicone emulsifier, a destablizing auxiliary emulsifier, water, non-volatile emollient, a coupling agent, an active antiperspirant component and ancillary agents such as perfume, coloring agents, etc. The silicone emulsifier is a cyclomethicone-dimethicone copolyol silicone fluid marketed by Dow Corning Corp. under the trademark DOW CORNING 3225C formulation. The contents of these two U.S. patents are incorporated herein by reference in their entirety.

Also to be noted is PCT (International application) Publication No. WO 92/05767. This patent document discloses a clear gel-type cosmetic product having a viscosity of at least about 50,000 cps at 21° C. and a refractive index of 1.3975–1.4025 at 21° C., and having an optical clarity better than 50 NTU (Nephelometric Turbidity Units) at 21° C., the product being an emulsion with a water phase having an active ingredient incorporated therein and with an oil phase. The refractive indices (measured at 5893 Å) of the water and oil phases match to within 0.0004. The oil phase includes an emulsifier which when properly mixed with the water phase component yields a water-in-oil emulsion, and the water phase includes one or a combination of various polar species such as water, propylene glycol, sorbitol and ethanol. The water phase includes the deodorant and/or antiperspirant active ingredient. The contents of this PCT (International application) Publication No. 92/05767 are incorporated herein by reference in their entirety.

While various cosmetic gel compositions, including antiperspirant and deodorant compositions, that are clear, are known, it is still desired to provide a clear cosmetic gel composition (e.g., clear antiperspirant and/or deodorant gel composition) having an increased amount of cosmetically active material (e.g., antiperspirant agent) and also having other materials providing advantageous cosmetic effects in the composition, while maintaining a clear composition; having reduced whitening and tack; and which is mild and has reduced skin irritation potential relative to commercially available products.

SUMMARY OF THE INVENTION

It is a first object of the present invention to provide a clear cosmetic gel composition (for example, a clear deodorant and/or antiperspirant gel composition) having increased amounts of cosmetically active ingredient (for example, deodorant active and/or antiperspirant active ingredients) therein, and a packaged product containing such cosmetic gel composition.

It is a further object of the present invention to provide a clear cosmetic gel composition and packaged product, wherein additional components, or additional amounts of these components, providing improved cosmetic effects, can be incorporated in the composition, while still maintaining a clear composition.

It is a further object of the present invention to provide a clear cosmetic (e.g., deodorant and/or antiperspirant) gel composition and packaged product, wherein the composition is mild (has lower skin irritation potential) as compared with commercially available products.

It is a further object of the present invention to provide a clear cosmetic (e.g., deodorant and/or antiperspirant) gel composition and packaged product, which has reduced residue, and causes a reduced amount of whitening after application.

It is a still further object of the present invention to provide a clear cosmetic (e.g., deodorant and/or antiperspirant) gel composition, and packaged product, which has improved cosmetic characteristics, including reduced tackiness after application.

It is a still further object of the present invention to provide a clear cosmetic (e.g., deodorant and/or antiperspirant) soft gel composition, and packaged product, which has an increased amount of active material while maintaining clarity, which has reduced whitening and residue, and which has reduced tack.

It is a still further object of the present invention to provide a clear cosmetic (e.g., deodorant and/or antiperspirant) gel composition, based on water-in-silicone oil emulsions, having increased amounts of cosmetically active ingredients therein while maintaining clarity, which is mild (has low skin irritation potential) as compared with commercially available products, and which has reduced whitening and residue, and decreased tackiness, after application.

It is a still further object of the present invention to provide a clear cosmetic (e.g., deodorant and/or antiperspirant) gel composition, based on water-in-silicone oil emulsions, having increased amounts of cosmetically active ingredients therein, and also having additional components (and/or additional amounts of other components) in the water and/or oil phase of the emulsion providing advantageous cosmetic effects (e.g., reduced whitening and reduced tack, silkier feel and a cool sensation, etc.), while maintaining clarity.

It is a still further object of the present invention to provide a method of forming, and of using, the clear cosmetic (e.g., deodorant and/or antiperspirant) gel compositions as discussed in connection with the foregoing objects.

According to a first aspect of the present invention, various of the foregoing objects are achieved through a clear cosmetic gel composition having (1) an aqueous phase containing water and at least one cosmetically active ingredient, and (2) an oil phase containing a high refractive index material (e.g., a material having a refractive index in a range of 1.40 to 1.50), the composition further including (3) at least one coupling agent to bring the aqueous phase and the oil phase into a homogeneous composition (that is, the at least one coupling agent causes the aqueous phase to be uniformly distributed throughout the oil phase) and (4) an alkoxylated, alkyl substituted siloxane surface active agent in an amount sufficient to form the composition into a water-in-oil emulsion, the composition being a water-in-oil emulsion and having a refractive index (prior to addition of fragrance) in a range of from about 1.4026 to about 1.4150. Preferably, the refractive index of the composition is in a range of from about 1.4050 to about 1.4150, especially from about 1.4050 to about 1.4085, and most preferably the refractive index of the composition is a range of from about 1.4060 to about 1.4080. Refractive index measurements were made using a Bausch and Lomb Abbe 3L Refractometer.

Addition of fragrance to the gel composition according to the present invention may increase the refractive index of the finished product. The refractive index referred to previously (e.g., a broadest range of 1.4026 to 1.4150) is the refractive index prior to incorporating fragrance in the composition.

By providing a composition having the specified refractive index, a composition containing more of the cosmetically active ingredients (in particular, more of the antiperspirant active ingredient such as an antiperspirant active salt, where the composition is a clear antiperspirant gel composition) can be achieved.

Moreover, this composition having the specified refractive index can also include high refractive index components, in either the oil phase or the aqueous phase, or additional amounts of high refractive index components, that provide advantageous cosmetic or other aesthetic effects. That is, conventional clear compositions have a relatively low refractive index. These relatively low refractive indices of conventional clear compositions of the water-in-oil emulsion type are due at least in part to the relatively low refractive indices of various conventionally used silicone fluids (e.g., around 1.3995), incorporated in the oil phase of these conventional compositions. This limits materials (and amounts) that can be included in the conventional composition such that the emulsion as a whole has the required relatively low refractive index. This limitation can be avoided according to the present invention, providing an increased degree of freedom in the choice of materials that can be incorporated in both the aqueous and oil phases of the composition of the present invention. For example, emollients having a higher refractive index can be incorporated in the oil phase and in the water phase, especially in the oil phase, of compositions according to the present invention, having the relatively high refractive index. Since antiperspirant active materials generally have high refractive indices, these can be incorporated in larger amounts in compositions of the present invention. Moreover, materials having a high refractive index, that can reduce tack and whitening of the composition, can be incorporated in the oil phase of the composition of the present invention.

Desirably, the composition according to the present invention has at least near refractive index matching between (1) the aqueous phase and at least one coupling agent, on the one hand, and (2) the oil phase and alkoxylated, alkyl substituted siloxane surface active agent, on the other.

In particular, preferably, according to the present invention, a difference between the refractive index of (1) the aqueous phase and at least one coupling agent, and (2) the oil phase and alkoxylated, alkyl substituted siloxane surface active agent, is less than 0.0005.

Compositions according to the present invention can be clear. For example, illustratively, the composition according to the present invention has an optical clarity better than approximately 50 NTU (Nephelometric Turbidity Units) at room temperature (20°–25° C.), preferably having a turbidity measurement of less than approximately 30 NTU, more preferably less than approximately 20 NTU. Turbidity measurements as discussed in the foregoing and discussed hereinafter, were made with an Orbeco-Hellige #965 Direct-Reading Turbidimeter.

Where the cosmetic gel composition of the present invention includes an antiperspirant active agent as the cosmetically active ingredient, with such agent being incorporated in the composition in an amount sufficient to reduce flow of perspiration when the composition is applied to a human, a clear antiperspirant gel composition can be formed. Various conventional antiperspirant active aluminum-containing salts, including (but not limited to) aluminum chlorhydrate and aluminum zirconium tetrachlorohydrex gly, can be utilized as the antiperspirant active agent. Thus, a clear antiperspirant gel composition can be achieved, according to the present invention.

The composition according to the present invention can be a soft gel, for example, having a viscosity in a range from about 75,000 cps to about 350,000 cps at room temperature (20°–25° C.). Such a soft gel can be incorporated in conventional dispensing packages (for example, dispensing packages having slots or pores on the top thereof for extruding the gel to the upper surface, for rubbing the composition on the skin from such upper surface).

Desirably, the oil phase of the cosmetic gel composition according to the present invention includes a volatile silicone fluid, a non-volatile silicone fluid and an emollient. Preferably, such emollient, which can be a silicone material (such as phenyl trimethicone), is the material of the oil phase having the high refractive index, and has a refractive index higher than that of the volatile silicone fluid and higher than that of the non-volatile silicone fluid (that is, this emollient is, desirably, a high refractive index emollient compatible with the silicone fluids of the oil phase).

According to another aspect of the present invention, the aqueous phase of the clear cosmetic gel composition further includes at least one polypropylene glycol. Illustratively, tripropylene glycol can be utilized as the polypropylene glycol. According to this aspect of the present invention, propylene glycol can be used in combination with the polypropylene glycols. Incorporation of the polypropylene glycol in the gel composition improves cosmetic properties, including a reduction of tack and a decrease in the whitening and in the residue after application of the composition. Moreover, compositions incorporating polypropylene glycol, particularly, tripropylene glycol, have improved mildness (that is, reduced skin irritation potential) relative to commercially available products.

The objectives according to the present invention are also achieved through the method of forming the cosmetic gel composition according to the present invention. In this method, an aqueous-based phase comprising water; a cosmetically active ingredient; and a coupling agent is formed. Also formed is an oil-based phase containing at least a high refractive index material (a material having a refractive index in the range of 1.40 to 1.50) and an alkoxylated, alkyl substituted siloxane surface active agent, and desirably other silicone fluids. The refractive index of the oil-based phase is determined, and, if necessary, adjusted to be in the range from about 1.4026 to about 1.4150, and the refractive index of the aqueous-based phase is determined and adjusted (if necessary) to differ from the refractive index of the oil-based phase by less than 0.0005. The aqueous-based phase is then mixed with the oil-based phase (for example, the aqueous-based phase is slowly added to the oil-based phase with turbulent agitation), and then additional additives, such as fragrance and color or other active ingredients, are added with mixing. The resulting emulsion is then passed through, for example, a colloid mill or other high shear emulsifier so as to provide a viscous gel, the gel then being transferred to a suitable applicator or container for use by the consumer. Desirably, according to the present invention the aqueous-based phase further includes polypropylene glycol, such as tripropylene glycol, providing advantages in the final product as discussed previously.

The compositions according to the present invention are used as conventional cosmetic gel compositions are used. For example, where the composition according to the present invention is a clear antiperspirant soft gel composition, packaged in a dispensing container having a top surface with slots or pores, the gel is extruded from the dispensing container through the slots or pores and applied to the skin (for example, in axillary regions of the human body) by rubbing the soft gel material extruded through the top surface of the container on the skin in the axillary region.

As a further aspect of the present invention, the dispensing container is a clear container, so as to exhibit the clarity of the composition of the present invention.

Accordingly, by the present invention, a clear cosmetic gel composition (for example, a clear antiperspirant gel composition, such as a clear antiperspirant soft gel composition) can be provided, having increased amounts of cosmetically active ingredients (such as antiperspirant active material) and having other high refractive index beneficial materials in the composition while maintaining clarity of the composition. The composition is easy to manufacture. The composition has improved tack, a cool sensation, a silky feel and imparts no white residue on dry down compared to commercially available products. Moreover, compositions of the present invention incorporating a polypropylene glycol component (especially tripropylene glycol) have improved mildness (have reduced skin irritation potential) as compared to commercially available products, and have improved cosmetic properties (including reduced tackiness) and reduced white residue upon application.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, the present invention is described primarily in connection with a clear soft gel antiperspirant composition. However, the present invention is not limited to soft gel compositions or to antiperspirant compositions. For example, compositions according to the present invention can be clear deodorant compositions. Moreover, depending on additional or other active ingredients included in the composition, the composition can also be an emollient composition, an analgesic (methyl salicylate) composition, a sunscreen composition, etc. Various active materials incorporated in cosmetic compositions are disclosed in U.S. Pat. No. 4,322,400 to Yuhas, the contents of which are incorporated herein by reference in their entirety.

Throughout the present specification, "active antiperspirant" and "active deodorant" materials are discussed. Both types of materials contribute to reduction of body (e.g., axillary) malodor. By reduction of body malodor, we mean that, generally, there is less body malodor after application of a composition to the person's skin as compared to the person's body malodor without application of the composition. Such reduction can be due to a masking of the malodor, absorption and/or chemical reaction of the malodorous material, reduction of levels of the bacteria producing the malodorous material, e.g., from perspiration, reduction of perspiration, etc. The antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacted with malodorous materials, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

A desired feature of the present invention is that a clear, or transparent, cosmetic gel composition (e.g., clear or transparent deodorant or antiperspirant gel composition) can be provided. The term clear or transparent (that is clarity), according to the present invention, is intended to connote its usual dictionary definition; thus, a clear, e.g., cosmetic gel composition of the present invention allows ready viewing of objects behind it. By contrast, a translucent composition allows light to pass through, but causes the light to be so scattered that it will be impossible to see clearly objects behind the translucent composition. Optical clarity of compositions of the present invention can be measured using a turbidimeter, and desirably is better than 50 NTU measured at room temperature (20°–25° C.).

The present invention contemplates a clear cosmetic gel composition which is a water-in-oil emulsion. The aqueous phase of this emulsion contains water and at least one cosmetically active ingredient, with the cosmetically active ingredient being in the composition in an amount so as to have a cosmetic effect. The oil phase of the emulsion includes a high refractive index material (a material having a refractive index in the range of 1.40–1.50), and desirably also includes silicone fluids, and preferably contains both volatile and non-volatile silicone fluids. The compositions according to the present invention also include at least one coupling agent to bring the aqueous phase and the oil phase into a homogeneous composition, and an alkoxylated, alkyl substituted siloxane surface active agent to provide a waterin-oil emulsion. According to this aspect of the present invention, the composition has a refractive index in a range from about 1.4026 to 1.4150. This range for the refractive index is higher than the maximum of the range described in PCT International Application Publication No. WO 92/05767. By utilizing a higher refractive index, in a range as disclosed in the present application, clarity of the composition can be maintained, while increased amounts of cosmetic active ingredient (e.g., antiperspirant active ingredient such as an antiperspirant aluminum-containing salt) can be incorporated in the composition; and high refractive index materials providing advantageous benefits to the composition can be incorporated in the aqueous and oil phases of the composition.

The material, incorporated in the oil phase, which has the high refractive index, desirably is an emollient, and preferably has a refractive index in the range of 1.43 to 1.47, most preferably 1.45 to 1.47.

Desirably, refractive indices of the mixture of aqueous phase and at least one coupling agent, on the one hand, and the mixture of the oil phase and alkoxylated, alkyl substituted siloxane surface active agent, on the other, match each other to within 0.0005; that is, a difference between (1) the refractive index of the mixture of aqueous phase and coupling agents and (2) the refractive index of the mixture of oil phase and alkoxylated, alkyl substituted siloxane surface active agent, is less than 0.0005.

An optically clear cosmetic (e.g., antiperspirant or deodorant) gel composition that is visually clear, and, like glass, allows for the viewing of the objects behind it, is achieved. In particular, a composition having an optical clarity better than 50 NTU at room temperature (20°–25° C.), preferably having a turbidity measurement less than 30 NTU, more preferably less than 20 NTU, can be achieved.

Moreover, the clear cosmetic gel composition of the present invention, which is in the form of a macro-emulsion as contrasted to a micro-emulsion, does not need to contain wax or gelling agents such as soaps, cellulosic materials or algenites. Furthermore, the composition according to the present invention does not require polydimethylcyclosiloxane, although the present compositions may contain this material.

The gel emulsions according to the present invention are stable and optically clear, are cosmetically elegant, and are capable of being delivered from a suitable applicator package. They are easily applied to the skin and have a smooth, silky feel and a cool sensation, yet are fast-drying and non-tacky. These compositions of the present invention may be prepared by a batch process, or a continuous or semi-continuous process, and the processes yield compositions which are stable, highly efficacious and possess excellent aesthetic qualities.

Where the composition is an antiperspirant gel composition, any of the known antiperspirant active materials can be utilized in the composition of the present invention. Suitable materials which may be mentioned by way of example include aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used. In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

Antiperspirant active materials can be, but are not limited to, the following:

Antiperspirant Actives
Astringent salt of aluminum
Astringent salt of zirconium
Aluminum bromohydrate
Aluminum chlorohydrate
Aluminum dichlorohydrate
Aluminum sesquichlorohydrate
Aluminum chlorohydrex PG
Aluminum dichlorohydrex PG
Aluminum sesquichlorohydrex PG
Aluminum chlorohydrex PEG
Aluminum dichlorohydrex PEG
Aluminum sesquichlorohydrex PEG
Aluminum chloride
Aluminum sulfate
Aluminum zirconium chlorohydrate
Aluminum zirconium trichlorohydrate
Aluminum zirconium tetrachlorohydrate
Aluminum zirconium pentachlorohydrate
Aluminum zirconium octachlorohydrate
Aluminum zirconium trichlorohydrex Gly
Aluminum zirconium tetrachlorohydrex Gly
Aluminum zirconium pentachlorohydrex Gly
Aluminum zirconium octachlorohydrex Gly
Buffered aluminum sulfate
Potassium alum
Sodium aluminum chlorohydroxy lactate The preferred antiperspirant materials include Rezal 36G, aluminum zirconium tetrachlorohydrate or aluminum chlorhydrate.

The amount of active component that can be used will vary with the particular active ingredient incorporated. As a general rule, an antiperspirant product should contain an active antiperspirant material in an amount anywhere from about 10% to about 35% by weight, of the total weight of the composition, more preferably from about 20% to about 30% by weight, of the total weight of the composition. The active antiperspirant material utilized in the compositions of the present invention can be pre-dissolved in water or in another solvent (for example, in propylene glycol), or can be in powdered form, and may be buffered or unbuffered. Preferably, the antiperspirant materials are present in solution in a solvent therefor.

Where a deodorant active material is utilized, any deodorant active material which can be dissolved in the aqueous phase can be utilized. Illustratively, the deodorant active material can be 2, 4, 4'-trichloro-2'-hydroxy diphenyl ether (triclosan), and/or benzethonium chloride. Where the deodorant ingredient is used in place of the antiperspirant active ingredient, a deodorant gel composition (rather than an antiperspirant gel composition) would be provided.

Amounts of cosmetically active ingredients incorporated are those sufficient to have a cosmetic effect. For example, where a deodorant active ingredient such as triclosan is incorporated, amounts thereof as conventionally used in the art can be incorporated in the composition according to the present invention.

The aqueous phase includes one or a combination of various polar species, and includes at least water (refractive index of 1.3333). Other polar species include polyhydric alcohols and derivatives thereof (e.g., esters and ethers thereof). Illustratively, water can be included in the composition in an amount in the range of 20% to 70% by weight, of the total weight of the composition.

At least one coupling agent is included in the composition of the present invention. Such coupling agent is illustratively (but not limited to) the following:
Ethyl alcohol
2-ethylhexanol
Ethylene carbonate
N-methylglucamine
Linear ethoxylated polymer of methanol
Ethylene glycol monoethyl ether
Diethylene glycol monoethyl ether
Propoxylated oleyl alcohol
Butyl stearate
Butyl myristate
Isopropyl alcohol
SD-40 alcohol
Mineral Spirits
PPG (2–8) myristyl ether
PPG (2–8) lauryl ether
Dipropylene glycol
Sorbitol
PPG (2–10) cetyl ether
PEG-6 diisopropyl adipate
Methoxy PEG-22 dodecyl-glycol copolymer
PEG-30 Glyceryl monoacetate sorbitol
PEG-3 oleyl ether phosphate
PEG-(2–5) oleyl ether
PPG-(2–5) lanolate
PPG-(2–8) isostearate
Propylene glycol (2) methyl ether
PPG-(2–3) methyl ether
PPG-14 butyl ether
Ethoxylated (2–20 moles) glucose
Propoxylated (2–20 moles) glucose
PPG-15 Stearyl ether
PPG-(5–20) methyl glucose ether
Isoprene glycol
Propylene carbonate
Glycerine This coupling agent acts to stabilize the emulsion and also acts as a clarifying agent. Moreover, various of these coupling agents, such as SD-40 alcohol, aid in drying and has a cooling effect, providing advantageous aesthetic properties for the composition.

The coupling agent is preferably a low molecular weight alcohol such as, but not limited to, an alcohol having from about 2 to about 10 carbon atoms, preferably from about 2 to about 4 carbon atoms; or a glycol such as, but not limited to, propylene glycol, ethylene glycol, isoprene glycol and dipropylene glycol; glycerine, sorbitol and/or propylene carbonate. The coupling agent can be one compound or a mixture of compounds.

Illustratively, the coupling agent is present in an amount of from about 10% to about 30% by weight, preferably from about 14% to about 25% by weight, of the total weight of the composition.

The oil phase according to the present invention is, desirably, a silicone oil phase, so as to provide a water-in-silicone oil emulsion. The total of oil phase and siloxane surface active agent preferably makes up from about 8% to about 30% by weight, of the total weight of the composition. This surface active agent is an emulsifier which, when properly mixed with the aqueous phase components, oil phase components and coupling agents, yields a water-in-oil emulsion. The oil phase is desirably a blend of liquids.

The oil phase can include, illustratively, a volatile silicone fluid such as cyclomethicone and a non-volatile silicone fluid such as dimethicone; however, the composition of the present invention need not include both the volatile and non-volatile silicone fluids. Where the composition includes the volatile silicone, it is preferred that such volatile silicone be a polydimethylcyclosiloxane, present in an amount up to about 18% by weight, of the total weight of the composition, preferably from about 4% to about 12% by weight, of the total weight of the composition. Preferred polydimethylcyclosiloxanes are those named cyclomethicones, exemplified by the formula $((CH_3)_2 SiO)_x$ where x is a number from about 4 to about 6. Preferred cyclosiloxanes are octamethylcyclotetrasiloxane (x=4), decamethylcyclopentasiloxane (x=5) and blends of tetramer and pentamer cyclomethicones. Commercial cyclosiloxanes which can be utilized as part of the composition of the present invention include, illustratively, Dow Corning 244 fluid, Dow Corning 245 fluid, Dow Corning 344 fluid and Dow Corning 345 fluid (from Dow Corning Corp.).

The oil phase preferably is a mixture of a volatile silicone fluid (such as cyclomethicone), a non-volatile silicone fluid (such as dimethicone), and a high refractive index compatible emollient such as phenyl trimethicone. This high refractive index emollient has a higher refractive index than that of the silicone fluids (volatile silicone fluid and/or non-volatile silicone fluid) of the oil phase.

The alkoxylated, alkyl substituted siloxane surface active agent is preferably, but not limited to, a dimethicone copolyol. An illustrative alkoxylated silicone-containing surfactant utilizable according to the present invention is cetyl dimethicone copolyol, referred to in U.S. Pat. No. 5,162,378 to Guthauser. Illustratively, the alkoxylated, alkyl substituted siloxane surface active agent is included in the composition in an amount of 0.2% to 2% by weight, of the total weight of the composition.

A specific cyclomethicone-dimethicone copolyol fluid which can be utilized to provide the alkoxylated silicone-containing surface active agent is a mixture of cyclomethicone and dimethicone copolyol designated as DC3225C from Dow Corning Corp. This is a polyether substituted silicone of cyclomethicone and dimethicone copolyol (refractive index (RI)=1.3994). This DC3225C, which is an emulsifying agent, is useful for preparing stable water-in-oil emulsions where a silicone makes up a large portion of the oil phase, and is a dispersion of a silicone surfactant (dimethicone copolyol) (10% by wt.) in cyclomethicone (Dow Corning 344 Fluid) (90% by wt.).

The mixture of cyclomethicone and dimethicone copolyol fluid is present in the composition, illustratively, in an amount of from about 4% to about 20% by weight, of the total weight of the composition.

Various materials incorporated in the water-based phase and in the oil-based phase, and their refractive indices (as measured using the Bausch and Lomb Abbe 3L Refractometer), are set forth in the following:

| Ingredient | RI at 21° C. |
|---|---|
| Water-based phase | |
| Al—Zr Tetrachlorohydrex GLY (Rexal 36G (conc) 46%) | 1.4185 |
| SD40 Alcohol | 1.3644 |
| PPG-10 Butanediol | 1.4510 |
| Propylene Glycol | 1.4334 |
| 1,3-Butylene Glycol | 1.4404 |
| Dipropylene Glycol | 1.4415 |

| Ingredient | RI at 21° C. |
|---|---|
| Propylene Carbonate | 1.4216 |
| Sorbitol (70%) | 1.4605 |
| Isoprene Glycol | 1.4422 |
| Tween 80 | 1.4725 |
| Carbowax PEG 200 | 1.4589 |
| Carbowax PEG 300 | 1.4650 |
| Carbowax PEG 400 | 1.4671 |
| Tween 20 | 1.4705 |
| Water (Deionized) | 1.3336 |
| Glycerine | 1.4743 |
| Oil-based phase | |
| Dimethicone (DC 200 (50cs)) | 1.4049 |
| Phenyl Trimethicone (DC 556) | 1.4614 |
| Polyisobutylene (Panalane L-14E) | 1.4592 |
| Diisopropyl adipate (Dermol DIA) | 1.4248 |
| Polydecene (Silkflo 362NF) | 1.4448 |
| Polydecene (Silkflo 364NF) | 1.4554 |
| Polydecene (Silkflo 366NF) | 1.4595 |
| Diisopropyl Sebacate (Pelemol DIPS) | 1.4337 |
| Octyl isononanoate (Dermol 89) | 1.4366 |
| Isostearyl Stearate (Estalon ISS) | 1.4565 |
| Dermol G-76 | 1.4988 |
| DC Q2-5220 | 1.4536 |
| DC 3225C | 1.3994 |

The composition according to the present invention can include additional cosmetically active ingredients such as emollients, humectants, antiseptics, antioxidants, chelating agents, ultraviolet absorbers, colorants, fragrances and preservatives, as known in the art, which ingredients include, but are not limited to, the following:

Emollients

| | |
|---|---|
| stearyl alcohol | Stearic acid |
| Glyceryl monoricinoleate | Isobutyl palmitate |
| Glyceryl monostearate | Isocetyl stearate |
| Sulphated tallow | Oleyl alcohol |
| Propylene glycol | Isopropyl laurate |
| Mink oil | Sorbitan Stearate |
| Cetyl alcohol | Hydrogenated Castor Oil |
| Stearyl stearate | Hydrogenated soy glycerides |
| Isopropyl isostearate | Hexyl laurate |
| Dimethyl brassylate | Decyl oleate |
| Diisopropyl adipate | |
| n-dibutyl sebacate | |
| Diisopropyl sebacate | |
| 2-ethyl hexyl palmitate | |
| Isononyl isononanoate | |
| Isodecyl isononanoate | |
| Isotridecyl isononanoate | |
| 2-ethyl hexyl palmitate | |
| 2-ethyl hexyl stearate | |
| D-(2-ethyl hexyl) adipate) | |
| Di-(2-ethyl hexyl) succinate | |
| Isopropyl myristate | |
| Isopropyl palmitate | |
| Isopropyl stearate | |
| Octacosanol | |
| Butyl stearate | |
| Glyceryl monostearate | |
| Polyethylene glycols | |
| Oleic acid | |
| Triethylene glycol | |
| Lanolin | |
| Castor oil | |
| Acetylated lanolin alcohols | |
| Acetylated lanolin | |
| Petrolatum | |
| Isopropyl ester of lanolin fatty acids | |
| Mineral oils | |
| Butyl myristate | |
| Isostearic acid | |
| Palmitic acid | |
| PEG-23 oleyl ether | |
| Olelyl Oleate | |
| Isopropyl linoleate | |
| Cetyl lactate | |
| Lauryl lactate | |
| Myristyl lactate | |
| Quaternised hydroxy alkyl aminogluconate | |
| Vegetable Oils | |
| Isodecyl oleate | |
| Isostearyl neopentanoate | |
| Myristyl myristate | |
| Oleyl ethoxy myristate | |
| Diglycol stearate | |
| Ethylene glycol monostearate | |
| Myristyl stearate | |
| Isopropyl lanolate | |
| Paraffin waxes | |
| Glycyrrhizic acid | |
| Hydrocyethyl stearate amide | |

Humectants

| | |
|---|---|
| Urea | Propylene glycol |
| Glycerin | Butylene glycol |
| Sorbitol | Ethyl hexanediol |
| Sodium 2-pyrrolidone-5-carboxylate | $C_{1-10}$ polyethylene glycols |
| | Hyaluronic acid |
| Soluble collagen | Lactic acid |
| Dibutyl phthalate | Sodium pyrrolidone carboxylate |
| Gelatin | Sodium lactate |
| Polyglycerogen | Orotic acid |

Antiseptics/Preservatives/Antioxidants/Chelating Agents

| | |
|---|---|
| Cetyl pyridinium chloride | |
| Tribromosalicylanilide | |
| Benzalkonium chloride | |
| Dehydroacetic acid | |
| Methyl paraben | |
| Propyl paraben | |
| Sodium dehydroacetate | |
| Quaternium-15 | |
| EDTA Benzyl alcohol | |
| Chlorobutanol | |
| Dichlorobenzyl alcohol | |
| Phenethyl alcohol | |
| Phenoxyethanol | 5-bromo-5-nitro-1, 3-dioxane |
| Propylene glycol | Glutaral |
| Chloroacetamide | Tocopherol |
| Imidazolidinyl urea | Zinc pyrithone |
| Butyl paraben | Sodium borate |
| Butylated Hydroxy Anisol | Boric acid |
| Ethyl paraben | Isobutyl paraben |
| | 2-(hydroxymethylamine)-ethanol |
| 5-chloro-2-methyl-4-isothiazolin-3-one | Paraformaldehyde |
| | Trimerosol |
| | Dodecyl gallate |
| 2-methyl-4-isothiazol-3-one | Hydroquinone |
| formaldehyde | Phenol |
| Butylated Hydroxy Toluene | Sodium pyritione |
| DMDM hydantoin | Stearalkonium chloride |
| 2-bromo-2-nitropropane-1,3-diol | |
| Sorbic acid | |
| Citric acid | |
| Triclosan | |
| Diazolidinyl urea | |
| Benzoic acid | |
| Propyl gallate | |
| Sodium benzoate | |
| potassium sorbate | |
| Chloroxylenol | |
| Tetrapotassium pyrophosphate | |
| Benzoxiquine | |
| Chlorobutanol | |
| Quaternium-11 | |
| U.V. absorber-1 | |
| Disodium phosphate | |
| Trisodium HEDTA | |

-continued

Benzethonium chloride
Sodium methyl paraben
DMHF
MDM hydantoin
O-phenylphenol
Chlorhexidine digluconate
Myristalkonium chloride
Ascorbylpalmitate
Isopropyl paraben
Quaternium-15
Benzylparaben
Phenyethyl alcohol
Phosphoric acid
Sodium O-phenyl phenate
Chlorhexidine dihydrochloride
Phenoxyisopropanol
Resorcinol
Dichlorophen, sodium salt
T-butyl hydroquinone
Dichlorophen
Methylbenzethonium chloride
Chlroacetamide
phenylmercuric acetate
Ascorbic acid
Benzyl benzoate
Hydantoin
Sodium sulfite
Sodium bisulfite
Iodine U.V. Absorbers

| | |
|---|---|
| 2-hydroxy-4-methoxybenzophenone | ethylhexylsalicylate |
| Octyl dimethyl p-aminobenzoic acid | Menthyl anthranilate |
| | p-dimethyl aminobenzoate |
| Digalloyl trioleate | |
| 2,2-dihydroxy-4-methoxy benzophenone | |
| Ethyl 4-[bis(hydroxypropyl)] aminobenzoate | |
| 2-ethylhexyl 2-cyano-3,3-diphenylacrylate | |
| Ethyl hexyl p-methoxy cinnamate2- | |
| Ethyl 4(bis(hydroxypropyl)) aminobenzoate | |
| 2-phenylbenzilnidazole-5-sulfonic acid | |
| Benzophenone-8 | |
| Benzophenone-6 | |
| Benzophenone-2 | |
| Benzophenone-1 | |
| Amyl dimethyl PABA | |
| Benzophenone-4 | |
| Benzophenone-9 | |

According to another aspect of the present invention, the aqueous phase further includes at least one polypropylene glycol, preferably tripropylene glycol. By including, e.g., tripropylene glycol in the composition, illustratively, in an amount in the range of 1% to 20% by weight, of the total weight of the composition, a clear cosmetic (e.g., antiperspirant) gel composition can be achieved, having desirable cosmetic properties such as reduced tack and reduced whitening.

While not being held to any theory, it is also thought that use of the glycol, especially a relatively high molecular weight glycol, e.g., tripropylene glycol, may reduce irritation potential by preventing other irritating agents from permeating into the skin, by preventing mechanical chafing of the skin through extended lubrication of the aluminum salt active particles on the skin surface, and, where appropriate, by avoiding any irritation by propylene glycol.

According to this aspect of the present invention, the aqueous phase can include a mixture of polypropylene glycol (e.g., tripropylene glycol) and propylene glycol. Where the composition includes a mixture of both tripropylene glycol and propylene glycol, the mixture illustratively can be included in the aqueous phase in an amount in the range of 1%–25% by weight, of the total weight of the composition.

While not limiting, in preferred embodiments the mixture of oil phase and alkoxylated, alkyl substituted siloxane surface active agent comprises from about 10% to about 30% by weight, of the total weight of the composition, and the combination of aqueous phase and coupling agents make up from about 70% to about 90% by weight, of the total weight of the composition.

In manufacturing the composition, and to provide an optically clear product (for example, an optically clear antiperspirant product), refractive indices of a mixture of oil phase and alkoxylated, alkyl substituted silicone surface active agent, on the one hand, and a mixture of the aqueous phase and the at least one coupling agent, on the other, are measured using a suitable refractometer such as a Bausch and Lomb Abbe 3L Refractometer, and the refractive index of one of these mixtures is adjusted as necessary in order to have a refractive index of one mixture that is within 0.0005 of the other mixture. In particular, in connection with antiperspirant compositions according to the present invention, the oil phase and alkoxylated, alkyl substituted silicone surface active agent are mixed and the refractive index of the mixture is optically measured. The aqueous phase is formulated using, inter alia, the active ingredient and water, and the coupling agent is mixed therewith and the refractive index of this mixture of aqueous phase and coupling agent is optically measured. If the two mixtures do not match within 0.0005, refractive indices of either mixture can be adjusted. Preferably, the mixture including the aqueous phase has its refractive index adjusted by adding a coupling agent or water to change the refractive index so that it matches the refractive index of the mixture of oil phase and surface active agent, to at least 0.0005, at 21° C. Adding the coupling agent to the aqueous phase increases the refractive index of the mixture, while adding water to the aqueous phase reduces the refractive index of the mixture. Following adjustment, the mixtures are again optically measured to verify sufficient matching of the refractive indices. The mixture of the aqueous phase and coupling agent is then slowly added to the mixture of the oil phase and alkoxylated, alkyl substituted siloxane surface active agent, with turbulent agitation; optionally, fragrance can then be added, and the mixture sheared (e.g., by passing the resulting emulsion through a colloid mill or other suitable high shear emulsifier) to form a stable water-in-oil emulsion with desired viscosities, illustratively, in excess of 40,000 cps at room temperature (20°–25° C.), preferably, between 75,000 and 350,000 cps, more preferably between 120,000 and 325,000 cps, most preferably between 200,000 and 325,000 cps.

After formation of the composition having the desired viscosity, the composition can then be packaged into conventional packages, using conventional techniques. For example, the gel can be introduced into a dispensing package (for example, a package having a top surface with slots or pores), as conventionally done in the art. Desirably, the dispensing package is a clear package, so as to exhibit the clear composition to the purchasing consumer.

Thereafter, the product can be dispensed from this dispensing package, by extruding the gel from the dispensing package onto the top surface, through the pores or slots, and then rubbing the exposed gel on the skin, (for example, on skin in the axillary regions), so as to deposit the active material (for example, antiperspirant active material) on the skin. This provides good deposition of the antiperspirant active material, as well as other active materials, on the skin.

In the following, specific examples of compositions within the scope of the various aspects of the present invention are set forth. These specific examples are illustrative of the present invention, and are not limiting. In the following examples, as well as throughout the present specification, where appropriate the names utilized are the CTFA (Cosmetics, Toiletry and Fragrance Association, Inc.) names, as set forth in the *CTFA International Cosmetic Ingredient Dictionary* (4th Ed. 1991), the contents of which dictionary are incorporated herein by reference in their entirety. Amounts of each of the ingredients is in percent by weight, of the total weight of the composition.

| | Examples 1–6 | | | | | |
|---|---|---|---|---|---|---|
| Example No.: | 1 | 2 | 3 | 4 | 5 | 6 |
| Ingredient | % | % | % | % | % | % |
| ALUMINUM ZIRCONIUM TETRACHLOROHYDREX GLY (REZAL 36G CONC (46%)) | 54.00 | 54.00 | 54.00 | 54.00 | 54.00 | 54.00 |
| SD ALCOHOL 40 | | 8.00 | 8.00 | 8.00 | 8.00 | 8.00 |
| DEIONIZED WATER | 10.92 | 8.90 | 9.83 | 10.92 | 12.26 | 7.18 |
| ISOPRENE GLYCOL | 9.06 | | | | | |
| PROPYLENE CARBONATE | 11.10 | | | | | |
| PROPYLENE GLYCOL | | | 10.17 | | | |
| DIPROPYLENE GLYCOL | | | | 9.08 | | |
| SORBITOL (70%) | | | | | 7.74 | |
| GLYCERINE | | | | | | 12.82 |
| CYCLOMETHICONE AND DIMETHICONE COPOLYOL (DC3225C) | 9.00 | 9.00 | 9.00 | 9.00 | 9.00 | 9.00 |
| DIMETHICONE 50cs (DC 200 50cs) | 7.93 | 7.93 | 7.93 | 7.93 | 7.93 | 7.93 |
| PHENYL TRIMETHICONE (DC 556) | 1.07 | 1.07 | 1.07 | 1.07 | 1.07 | 1.07 |

| | Examples 7–9 | | |
|---|---|---|---|
| Example No. | 7 | 8 | 9 |
| Ingredient | % | % | % |
| Phenyltrimethicone | 1.07 | 1.07 | 1.07 |
| Dimethicone copolyol and cylomethicone (DC 3225C) | 9.00 | 9.00 | 9.00 |
| dimethicone 50 cst | 7.93 | 7.93 | 7.93 |
| Aluminum Zirconium tetrachlorohydrex GLY (46% solution) | 54.00 | 54.00 | 54.00 |
| Ethanol (95%) | 8.00 | 8.00 | 8.00 |
| Deionized Water | 10.92 | 8.83 | 9.31 |
| Dipropylene glycol | 9.08 | | |
| Tripropylene glycol | | 11.17 | |
| PPG-425 | | | 10.69 |
| Total | 100.00 | 100.00 | 100.00 |

| | Examples 10–13 | | | |
|---|---|---|---|---|
| Example No. | 10 | 11 | 12 | 13 |
| Ingredients | % | % | % | % |
| Aluminum-Zirconium Tetrachlorohydrex GLY (46%) (REZAL 36G concentrate) | 54.00 | 48.00 | 48.00 | 54.00 |
| SD 40 Alcohol | 8.00 | 8.00 | 8.00 | 8.00 |
| Deionized Water | 9.20 | 11.90 | 11.50 | 8.83 |
| Propylene Glycol | 10.20 | 6.00 | 10.20 | — |
| Tripropylene Glycol | — | 7.50 | 3.70 | 11.17 |
| Cyclomethicone & Dimethicone Copolyol (DC3225C) | 9.00 | 9.00 | 9.00 | 9.00 |
| Dimethicone 50 cs (DC 200) | 7.25 | 7.25 | 7.25 | 7.30 |
| Phenyl Trimethicone (DC 556) | 1.75 | 1.75 | 1.75 | 1.70 |
| Fragrance | 0.60 | 0.60 | 0.60 | — |
| Total | 100.00 | 100.00 | 100.00 | 100.00 |

In the foregoing Examples 10–12, the refractive index of each composition without the fragrance, was 1.4075.

Thus, according to the present invention, a clear cosmetic gel composition, which can be a soft gel, containing increased amounts of the cosmetically active ingredient (e.g., increased amounts of the antiperspirant active ingredient, where the composition is an antiperspirant gel composition), and also containing in both the oil phase and the aqueous phase high-refractive index materials providing cosmetic benefits, can be achieved, while maintaining clarity of the composition. This composition can be extruded through pores or slots of a conventional soft solid or soft gel dispensing container. The compositions are stable, even in the presence of conventional antiperspirant active aluminum-containing salts such as aluminum chlorohydrate or aluminum-zirconium tetrachlorohydrex-GLY. Compositions according to the present invention can be easily and simply manufactured. Moreover, the composition according to the present invention has reduced whitening and leaves a decreased residue after application, and has reduced tack. In addition, compositions according to the present invention have reduced skin irritation potential as compared to comparable commercial products.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A clear cosmetic gel composition, comprising:
   (a) an aqueous phase containing (i) water and (ii) at least one cosmetically active ingredient in an amount so as to have a cosmetic effect;
   (b) an oil phase comprising a volatile silicone fluid and a non-volatile silicone fluid, the oil phase including a material having a refractive index in the range of 1.40 to 1.50;
   (c) at least one coupling agent in an amount of 10% to 30% such that the aqueous phase is uniformly distributed in the oil phase; and
   (d) an alkoxylated, alkyl substituted siloxane surface active agent which is dimethicone copolyol in an amount in the range of 0.2–2.0% so as to form a water-in-oil emulsion, wherein said cosmetic gel composition is a water-in-oil emulsion, wherein a refractive index of the composition is in a range of from about 1.4050 to 1.4085, and wherein the percents are based on the total weight of the composition.

2. A clear cosmetic gel composition according to claim 1, wherein said refractive index is in a range of from 1.4060 to about 1.4080.

3. A clear cosmetic gel composition according to claim 1, wherein each of a mixture of the aqueous phase and coupling agent, and (2) a mixture of the oil phase and dimethicone copolyol, has a refractive index, with a difference between the refractive index of the mixture (1) and the refractive index of the mixture (2) being less than 0.0005.

4. A clear cosmetic gel composition according to claim 3, wherein said emulsion has an optical clarity better than 50 NTU.

5. A clear cosmetic gel composition according to claim 1, wherein said cosmetically active ingredient is an antiperspirant active agent in an amount of 10% to 35% by weight based on the total weight of the composition.

6. A clear cosmetic gel composition according to claim 5, wherein said clear cosmetic gel composition is a clear antiperspirant gel composition comprising an antiperspirant active agent incorporated in the composition in an amount sufficient to reduce flow of perspiration when the composition is applied to a human.

7. A clear antiperspirant gel composition according to claim 6, wherein a sum of the amount of the dimethicone copolyol and the oil phase is from about 8% to about 30% by weight, of the total weight of the composition.

8. A clear antiperspirant gel composition according to claim 7, wherein the composition is a soft gel.

9. A clear antiperspirant gel composition according to claim 6, wherein the composition has a viscosity in a range of from about 75,000 to about 350,000 cps at room temperature (20°–25°).

10. A clear antiperspirant gel composition according to claim 7, wherein said emollient has a higher refractive index than that of said volatile silicone fluid and that of said non-volatile silicone fluid.

11. A clear antiperspirant gel composition according to claim 6, wherein a sum of the amount of aqueous phase and of the at least one coupling agent is 70%–90% by weight, of the total weight of the composition, and a sum of the amount of the oil phase and dimethicone copolyol is 10%–30% by weight, of the total weight of the composition.

12. A clear antiperspirant gel composition according to claim 11, wherein the aqueous phase further includes at least one component selected from the group consisting of polypropylene glycols.

13. A clear antiperspirant gel composition according to claim 12, wherein the at least one component includes tripropylene glycol.

14. A packaged antiperspirant gel composition, comprising the composition of claim 13 in a clear package.

15. A clear antiperspirant gel composition according to claim 6, wherein the aqueous phase further includes at least one component selected from the group consisting of polypropylene glycols.

16. A clear antiperspirant gel composition according to claim 15, wherein the at least one component includes tripropylene glycol.

17. A clear cosmetic gel composition according to claim 1, wherein the aqueous phase further includes at least one component selected from the group consisting of polypropylene glycols.

18. A clear cosmetic gel composition according to claim 17, wherein the at least one component includes tripropylene glycol.

19. A clear cosmetic gel composition according to claim 1, wherein the cosmetically active ingredient includes at least one deodorant active agent, in an amount so as to provide a deodorizing function, whereby a clear deodorant gel composition is provided.

20. A clear antiperspirant soft gel composition made by combining:
   (a) an antiperspirant active ingredient, in an amount sufficient to reduce flow of perspiration from a human;
   (b) water;
   (c) at least one coupling agent;
   (d) a volatile silicone fluid;
   (e) a non-volatile silicone fluid;
   (f) an emollient, the emollient having a refractive index in the range of 1.40–1.50; and
   (g) dimethicone copolyol;
wherein components (a)–(g) are a water-in-oil emulsion, the emollient is in the oil phase, and the composition has a refractive index in a range from 1.4050 to 1.4085.

21. A clear antiperspirant soft gel composition according to claim 20, wherein the composition is made by combining, in percent by weight of the total weight of the composition, 8%–30% in total of components (d)–(g), said 8%–30% including 0.2%–2.0% of said dimethicone copolyol, and 10%–30% of said one coupling agent.

22. A clear antiperspirant soft gel composition according to claim 21, wherein the antiperspirant active ingredient is added in the composition in an amount of from about 10% to about 35% by weight, of the total weight of the composition.

23. A clear antiperspirant soft gel composition according to claim 22, wherein the emulsion has an optical clarity better than 50 NTU.

24. A clear antiperspirant soft gel composition according to claim 23, wherein components (a)–(c) form a mixture having a first refractive index and components (d)–(g) form a mixture having a second refractive index, a difference between the first refractive index and the second refractive index being less than 0.0005.

25. A clear antiperspirant soft gel composition according to claim 24, wherein the composition has a viscosity in a range of from about 75,000 to about 350,000 cps at room temperature (20°–25° C.).

26. A clear cosmetic gel composition, comprising:
   (a) an aqueous phase containing (i) water, (ii) at least one cosmetically active ingredient, in an amount so as to have a cosmetic effect, and (iii) at least one polypropylene glycol;
   (b) an oil phase;
   (c) at least one coupling agent such that the aqueous phase is uniformly distributed in the oil phase; and
   (d) dimethicone copolyol in an amount so as to form a water-in-oil emulsion, wherein said cosmetic gel composition is a water-in-oil emulsion.

27. A clear cosmetic gel composition according to claim 26, wherein said at least one polypropylene glycol includes tripropylene glycol.

28. A clear cosmetic gel composition according to claim 27, wherein the aqueous phase further includes propylene glycol.

29. A clear cosmetic gel composition according to claim 26, wherein the oil phase includes silicone fluids.

* * * * *